Oct. 4, 1938. E. P. DONOHER Re. 20,871

SUPPORT AND HAIR COVERING FOR EARPHONES

Original Filed Dec. 11, 1934

INVENTOR

Edith P. Donoher,

Robert J. Dennison

ATTORNEY

Reissued Oct. 4, 1938

Re. 20,871

UNITED STATES PATENT OFFICE 20,871

SUPPORT AND HAIR COVERING FOR EARPHONES

Edith P. Donoher, Los Angeles, Calif.

Original No. 2,040,246, dated May 12, 1936, Serial No. 757,053, December 11, 1934. Application for reissue January 6, 1938, Serial No. 183,687

12 Claims. (Cl. 181—25)

The present invention relates to improvements in acoustic devices and has reference more particularly to an auricle adapted to be worn upon the person of those whose hearing is defective, the auricle aiding such partially deaf persons to hear more distinctly.

The primary object of the present invention is to provide a hair covering for earphones or auricles, so that the earphones will not be visible while being worn, the hair covering attachment having means associated therewith for supporting the earphones or auricles in position.

Another important object of the invention is to provide a support and hair covering for an earphone of the above-mentioned character which can be readily and easily attached to or removed from the head of the wearer, the device causing no discomfort to the wearer when attached.

A still further object of the invention is to provide a hair covering for an earphone wherein natural or artificial hair, matching the hair of the person using the earphone, is employed as a covering for the earphone, means being associated with the covering to facilitate the reception and support of an earphone or auricle and further permitting the device to be supported in proper position on the head of the wearer, the hair covering concealing the earphone so that the same is not visible while being worn.

Other objects and advantages of the present invention will become apparent from the following description when taken in connection with the accompanying drawing.

In the drawing, wherein like references designate corresponding parts throughout the several views.

Figure 1:
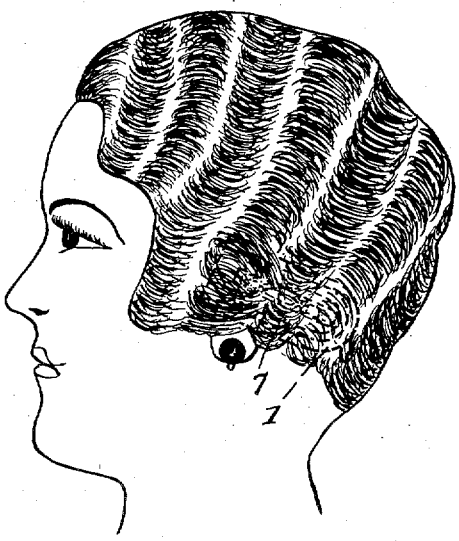
Figure 1 is a side elevation showing the hair covering attached to the head of the wearer and concealing the earphone.

In the drawing, wherein for the purpose of illustration is shown the preferred embodiment of my invention, the numeral 1 designates generally my improved device, same comprising an elongated chamber or pocket 2 formed of any suitable fabric material.

This pocket comprises a front side 3 and a rear side 4. One piece of double net is preferably employed to form this pocket, although I do not wish to limit myself to the manner in which the pocket may be constructed. As clearly shown in the drawing, the pocket is open only at its forward end.

An ear trumpet or auricle denoted generally by the numeral 5 is removably arranged within the pocket 2 so that the bell or receiver portion of the trumpet is positioned adjacent the open forward end of the pocket and the laterally extending tip 6 associated with the smaller end of the horn of the earphone is disposed through a suitable opening provided therefor in the rear side 4 of the pocket 2 also adjacent the open forward end of said pocket.

The construction of the ear trumpet or auricle per se forms no part of the present invention, and this element may be of any suitable construction known to the art.

The tip 6 is adapted to extend into the passage of the ear, the outer end of the tip being open to permit the sound waves entering the passage of the ear, from which passage said sound waves travel through the petromastoid portion of the temporal bone.

Forming a salient part of the present invention is the hair covering 7 that is applied to the outer face of the pocket 2 in any suitable manner. Preferably, ventilated hair work, natural or artificial hair is employed as the covering material for the pocket to match the hair of the wearer of the device. The hair completely covers the outer side face of the pocket 2 and extends beyond the marginal edges.

A hair fastener of any well known type is secured to the outer face of the pocket 2 in any suitable manner. This hair-fastening unit 8 may extend in any position with respect to the pocket and the purpose thereof will be presently described. A similar hair-fastening unit 9 is secured to the rear side of the pocket 2 adjacent the closed end thereof and as is clearly shown in Figure 2 of the drawing. This hair-fastening unit 9 may also be disposed at any desired angle. In the instant illustration, I have shown the hair fastener in the form of a barrette, although I do not wish to limit myself solely to use of such type of hair fastener. It may be a clamp-pin, spring clip, or any device which will clamp a strand of hair securely. All clamps may be attached either to covering or to the auricle.

The hair fastening units are preferably secured in their respective positions by stitching, although any other suitable securing means may be provided to attach the clamps to the pocket or auricle.

I wish also at this time to mention that if desired, the bell or mouth of the earphone A may be formed with a series of small openings to facilitate securing of the mouth of the earphone or auricle to the open end of the pocket 2 by stitching. A net or hair arrangement may also cover the mouth of the earphone.

Figure 2:
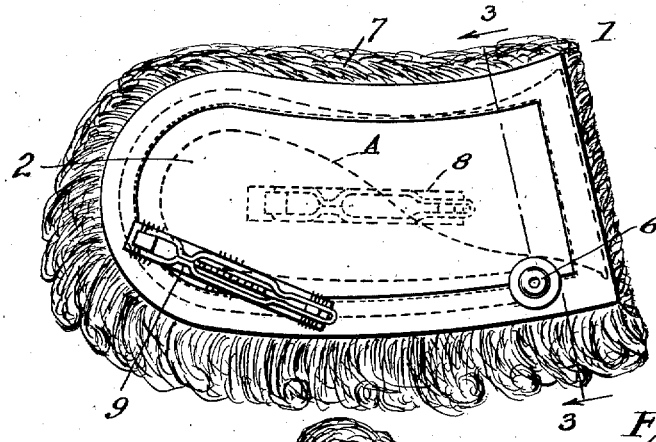
Figure 2 is an elevational view of the pocket for the earphone and the hair covering therefor, looking at the inner or rear side thereof.
Figure 3:
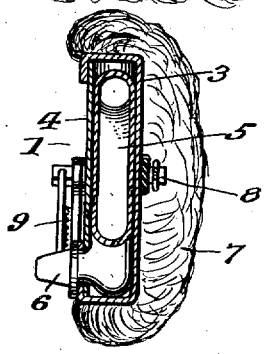
Figure 3 is a transverse section taken approximately on the line 3—3 of Figure 2, showing the relationship of the several parts with respect to the earphone or auricle arranged in the pocket of the device.

In use, the earphone or auricle A is positioned or secured within the pocket 2 in a manner as shown in dotted lines in Figure 2 of the drawing or in any other angle on the head. The tip 6 is inserted in the canal of the ear and the device is secured against the head of the wearer by arranging strands of the wearer's hair over the device and securing such strands to the hair fastener 8. In a similar manner, some of the strands of the wearer's hair are brought to the rear end portion of the device and are held by the hair fastener 9. The hair fasteners 8 and 9 will positively support the earphone and the covering therefor in proper position on the head of the wearer and the hair covering 7, being of the same color as the natural hair of the wearer, the earphone and its covering will be entirely concealed from view and this without presenting any unsightly appearance.

By employing the barrettes, combs, clamps, pins, etc., 8 and 9 to support or suspend the device in position against the ear, the use of head bands to support the earphone is obviated.

If desired, however, a head band may be employed to support the earphone and its covering in addition to the hair fasteners and to this end, any appropriate separable fastening means may be associated with the free end of the head band and the inside side face of the pocket 2. The head band is a flat spring steel band, ¼ inch wide to extend over the crown of the head and is adjustable in length. Each end of the band may have a screw hole for attaching the same to the outside of the auricle permitting adjustment of the auricle to any angle at side of head. The lower end of the band is insertable in a pocket in the covering, thus preventing the band from slipping too far forward or backward on the head.

In Figure 1 of the drawing, I have illustrated one position of the earphone and covering therefor in dotted lines and there is further shown in this particular figure, one position that the device assumes when being worn and the manner in which the hair of the person wearing the device actually conceals the earphone and its covering.

The hair-line is left for the individual wearer to select. It may be fringe, or curls or any other finish and may be of any length desired.

While I have shown the preferred embodiment of the invention, it is to be understood that minor changes in the size, shape and arrangement of parts may be resorted to without departing from the spirit of the invention and the scope of the appended claims.

Having thus described the invention, what I claim is:

1. In a device for supporting an earphone, a member adapted to receive and support an earphone, hair-fastening elements on opposite sides of said member for clamping engagement with the hair of the wearer to removably support the device in any position against the ear.

2. In a device of the class described, a member adapted to receive and support an earphone, hair-fastening elements on opposite sides of said member for clamping engagement with the hair of the wearer to removably support the device in position against the ear, and a hair covering carried by the member for concealing the device and the earphone therein when in use.

3. In a device of the class described, a fabric pocket-forming member adapted to entirely receive and conceal an earphone, hair-fastening elements on opposite sides of the pocket-forming member for clamping engagement with the strands of the hair of the wearer to removably support the pocket-forming member and the earphone therein in position against the ear of the person.

4. In a device of the class described, a fabric pocket-forming member adapted to receive an earphone, hair-fastening elements for clamping engagement with the strands of the hair of the wearer to removably support the pocket-forming member and the earphone therein in position against the ear of the person, and a hair covering applied to the outer side of said pocket adapted to match the hair of the wearer to conceal the device when in use.

5. In a device of the class described, a fabric pocket open at one end and adapted to receive an earphone, the inner side of the pocket having an opening to accommodate the ear canal engaging tip of said earphone, fastening devices on both sides of the pocket for clamping strands of the hair of the wearer to removably support the pocket and the earphone in any position against the ear of the person, and a hair covering applied to the outer side of the pocket and adapted to match the hair of the wearer for concealing the pocket and the earphone from view when the device is in use.

6. In a device for supporting an earphone, a member adapted to receive and support an earphone, a hair-clamping element secured to said member for clamping a strand of the hair of the wearer to removably support the device in any position by the strand of hair.

7. In a device of the class described, a member adapted to receive and support an earphone, hair-clamping elements on said member for clamping the hair of the wearer to removably support the device by the hair, and a hair covering carried by said member for concealing the device when in use.

8. In a device of the class described, a fabric pocket-forming member adapted to entirely receive and conceal an earphone, hair-fastening elements on said pocket-forming member for clamping engagement with a strand of the hair of the wearer to removably support said pocket-forming member and said earphone.

9. In a device of the class described, a fabric pocket-forming member adapted to receive an earphone, a hair-fastening element for clamping engagement with a strand of the hair of the wearer to removably support said pocket-forming member and said earphone, and a hair covering applied to the outer side of said pocket for concealing the device when in use.

10. In an acoustic device adapted to be worn by a person with defective hearing, an acoustic element and a clamp secured to said element for engagement with the hair of the wearer to removably suspend the weight of the device in any position by the hair.

11. In an acoustic device adapted to be worn by a person with defective hearing, an acoustic element, a clamp secured to said element for engagement with the hair of the wearer to removably suspend the weight of the device in any position by the hair, and a hair covering carried by said device for concealing the device when in use.

12. In an acoustic device adapted to be worn by a person with defective hearing, an acoustic assembly comprising an acoustic element and a covering therefor, and a fastening member secured to said acoustic assembly, said fastening member being constructed and arranged for suspending the weight of the device on the head, said covering comprising hair for concealing the device when in use.

EDITH P. DONOHER.